(12) United States Patent
Kottgen et al.

(10) Patent No.: US 8,722,338 B2
(45) Date of Patent: May 13, 2014

(54) MODULATION OF ABCG2-MEDIATED URATE TRANSPORT TO TREAT HYPERURICEMIA AND GOUT

(75) Inventors: Michael Kottgen, Freiburg (DE); Josef Coresh, Pikesville, MD (US); William Guggino, Baltimore, MD (US); Anna Kottgen, Freiburg (DE); Owen Woodward, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 212 days.

(21) Appl. No.: 13/255,601

(22) PCT Filed: Mar. 11, 2010

(86) PCT No.: PCT/US2010/026932
§ 371 (c)(1),
(2), (4) Date: Sep. 9, 2011

(87) PCT Pub. No.: WO2010/114686
PCT Pub. Date: Oct. 7, 2010

(65) Prior Publication Data
US 2012/0010102 A1    Jan. 12, 2012

Related U.S. Application Data

(60) Provisional application No. 61/159,154, filed on Mar. 11, 2009.

(51) Int. Cl.
*C12Q 1/68* (2006.01)
(52) U.S. Cl.
USPC ................ 435/6.13; 435/8; 435/10; 424/9.2; 530/350

(58) Field of Classification Search
None
See application file for complete search history.

(56) References Cited

U.S. PATENT DOCUMENTS

| | | |
|---|---|---|
| 7,138,493 B1 | 11/2006 | Dean et al. |
| 2004/0014087 A1 | 1/2004 | Hodgson et al. |
| 2008/0145313 A1 | 6/2008 | Watson et al. |
| 2009/0155228 A1* | 6/2009 | Nagy et al. ................. 424/93.7 |

FOREIGN PATENT DOCUMENTS

| | | |
|---|---|---|
| WO | WO 95-00157 A1 | 1/1995 |
| WO | WO 2004-113558 A1 | 12/2004 |

OTHER PUBLICATIONS

Zhang et al., "Identification of inhibitors of ABCG2 by a bioluminescence imaging-based high-throughput assay", Cancer Res 2009; Jul. 15, 2009, 69 (14), pp. 5867-5875.

\* cited by examiner

*Primary Examiner* — Jim Ketter
(74) *Attorney, Agent, or Firm* — Jeffrey W. Childers

(57) ABSTRACT

Genome-wide association studies (GWAS) was recently used to identify SNPs in a genomic region on chromosome 4 that associate with serum urate levels and gout. The present disclosure shows that human ATP-binding cassette, subfamily G, 2 (ABCG2), encoded by the ABCG2 gene contained in this region, is a hitherto unknown urate efflux transporter. The present disclosure further shows that native ABCG2 is located in the brush border membrane of kidney proximal tubule cells, where it mediates renal urate secretion. Introduction of the mutation Q141K encoded by the common SNP rs2231142 by site-directed mutagenesis resulted in reduced urate transport rates compared to wild-type ABCG2. Data from a population-based study of 14,783 individuals support rs2231142 as the causal variant in the region and show highly significant associations with urate levels and gout.

28 Claims, 6 Drawing Sheets

MODULATION OF ABCG2-MEDIATED URATE TRANSPORT TO TREAT HYPERURICEMIA AND GOUT

CROSS-REFERENCE TO RELATED APPLICATIONS

This application is a 35 U.S.C. §371 U.S. national entry of International Application PCT/US2010/026932 having an international filing date of Mar. 11, 2010, which claims the benefit of U.S. Provisional Application No. 61/159,154, filed Mar. 11, 2009, the content of each of the aforementioned applications is herein incorporated by reference in its entirety.

FEDERALLY SPONSORED RESEARCH OR DEVELOPMENT

This invention was made with United States Government support under grant nos. N01-HC-55015, N01-HC-55016, N01-HC-55018, N01-HC-55019, N01-HC-55020, N01-HC-55021, N01-HC-55022, R01HL087641, R01HL59367 and R01HL086694 awarded by the National Institutes of Health (NIH); contract no. U01HG004402 awarded by the National Human Genome Research Institute; and contract no. HHSN268200625226C awarded by the National Institutes of Health. Infrastructure was partly supported by Grant Number UL1RR025005, a component of the National Institutes of Health and NIH Roadmap for Medical Research. The functional studies were supported by R01DK32753 awarded by the National Institutes of Health (NIH). The United States Government has certain rights in the invention.

TECHNICAL FIELD

Methods of screening for activators of urate efflux transporters, including human ATP-binding cassette, sub-family G, 2 (ABCG2) and variants thereof.

BACKGROUND

Urate is the end product of purine metabolism in humans. Humans and higher primates have much higher serum urate levels than other species because they lack the enzyme uricase, which converts urate into its breakdown product allantoin. See Anzai N., et al., "New insights into renal transport of urate," *Curr. Opin. Rheumatol.* 19:151-157 (2007). Reduced excretion of urate by the kidney is the main cause for elevated urate levels, Anzai et al., supra, which can lead to gout, a painful condition affecting approximately three million individuals in the United States. See Lawrence R. C., et al., "Estimates of the prevalence of arthritis and other rheumatic conditions in the United States, Part II," *Arthritis Rheum.* 58:26-35 (2008).

It is well established that gout is a consequence of elevated serum urate levels. Anzai et al., supra. Yet, medications used to decrease serum urate levels are frequently not effective. Allopurinol, the most commonly used drug to decrease serum urate levels, inhibits the production of urate. Elevated serum urate levels, however, are usually a consequence of impaired renal urate excretion rather than increased urate production.

Renal urate transport is complex and still poorly understood. Anzai et al., supra. Although multiple renal urate transporters have been characterized in model systems, their role in human disease is mostly unclear. To date, it has been difficult to target renal urate secretion pharmacologically, because the molecular identity of the transporters mediating secretion in humans was not known.

Serum urate levels are highly heritable, suggesting a strong genetic component. See Yang Q., et al. "Genome-wide search for genes affecting serum uric acid levels: The Framingham Heart Study," *Metabolism* 54:1435-1441 (2005). In a genome-wide association study (GWAS) of serum urate levels, multiple single-nucleotide polymorphisms (SNPs) in a genomic region on chromosome 4 containing the ATP-binding cassette subfamily G member 2 (ABCG2) gene were identified as being associated with urate levels and prevalence of gout. See Dehghan A., et al., "Association of three genetic loci with uric acid concentration and risk of gout: a genome-wide association study," *Lancet* 372:1953-1961 (2008). ABCG2 was first identified as a multidrug resistance protein, see Doyle L. A., et al., "A multidrug resistance transporter from human MCF-7 breast cancer cells," *Proc. Natl. Acad. Sci. USA* 95:15665-15670 (1998), and has been shown to transport a wide range of structurally and functionally diverse substrates, such as chemotherapeutics. See Polgar O., et al., "ABCG2: structure, function and role in drug Response," *Expert Opin. Drug Metab. Toxicol.* 4:1-15 (2008). Yet, the physiological substrate and the roles of ABCG2 in vivo have remained elusive.

SUMMARY

The screening methods of the present invention provide rapid screening and identification of novel activators of ABCG2. Such assays are also beneficial for screening for activators of mutant ABCG2 transporters that are expressed in subjects with hyperuricemia or gout. It is contemplated that such methods will be useful in identifying therapeutic agents specifically tailored to treat an individual patient.

More specifically, the present invention provides screening methods to identify agents that can activate, enhance, or otherwise increase urate transport by ABCG2. It is contemplated that the screening methods will be automated to provide high-throughput screening of candidate agents. For example, in some embodiments, the methods comprise the simultaneous screening of multiple agents with potential ABCG2 activating activities. This may be achieved by addition of reagents/components of the assay using robotic fluid delivery; the analysis of multiple samples in multi-well formats; using a fluorescent plate reader, as well as other automation methods known in the art. Other examples of methods of automated equipment and assay procedures for membrane-associated proteins are described in U.S. Pat. No. 6,127,133 and U.S. Pat. No. 5,670,113.

The ABCG2 protein may be an endogenously expressed transporter or an exogenously expressed transporter. Recombinant DNA technology may be used to express the ABCG2 transporter exogenously in a cell using methods of molecular biology as are known to one of skill in the art. One of skill in the art would be well equipped to construct an expression vector that expresses nucleic acids encoding the ABCG2 transporter using standard molecular biology techniques.

In another embodiment, there is provided a method of screening for agents that can activate the activity of ABCG2 comprising (a) providing a cell that expresses ABCG2; (b) exposing the cell to urate; (c) exposing the cell to an agent that is a candidate ABCG2 transporter activator; (d) measuring the transport of urate; and (e) comparing the transport of urate in the cell to the transport of urate in a cell that has not been exposed to the agent, thereby determining if the agent is an activator of activity of ABCG2. Other specific embodiments of the screening methods are described below and in the claims.

The method may further comprise the use of a fluorescent plate reader to provide high-throughput screening of agents. The method may be an in vitro method or an in vivo method, for example, using transgenic animals. It is contemplated that one may use animals, such as mice, as the genetics of this system, as well as methods for establishing transgenics are well known in this animal. Animals expressing ABCG2 can be provided with candidate agents and the transport of urate or other substrates can be imaged in vivo or in situ. General methods for in vivo imaging are described in Herrera and Banner (1990), and in Herrera et al., (1990). In situ methods for analysis are exemplified by the work by Ullrich and colleagues (Pietruck and Ullrich, 1995; Rohlicek and Ullrich, 1994). These methods may be suitably modified with the other teachings of the specification. The present invention contemplates the use of these methods in conjunction with the screening methods described herein.

The present invention further relates to methods that identify the presence of the ABCG2 single nucleotide polymorphism (SNP) rs2231442 in a subject and correlating the presence of such SNP to a subject's risk of developing gout and/or hyperuricemia.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE SEVERAL VIEWS OF THE DRAWINGS

Figure 3:
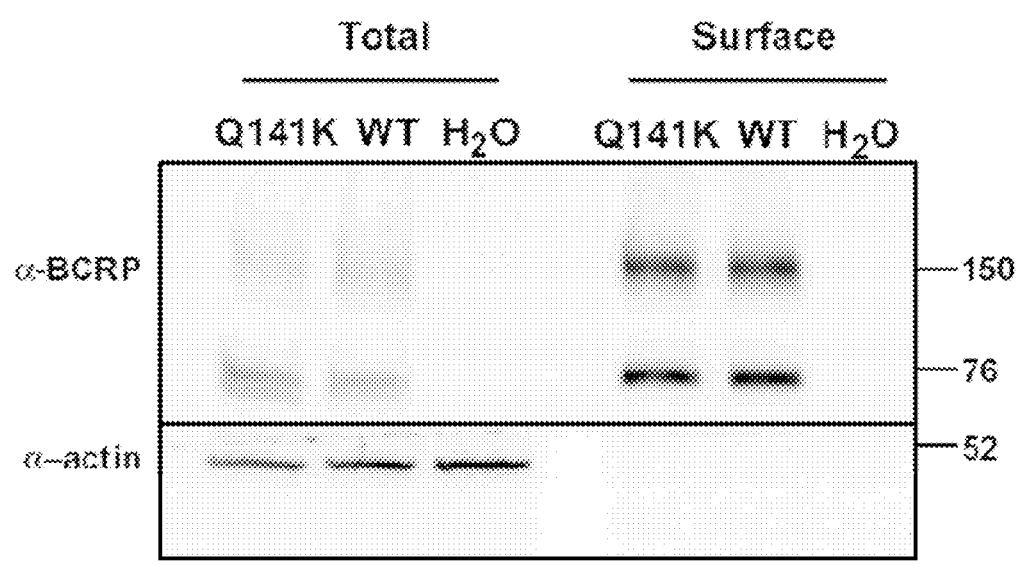
Figure 5:
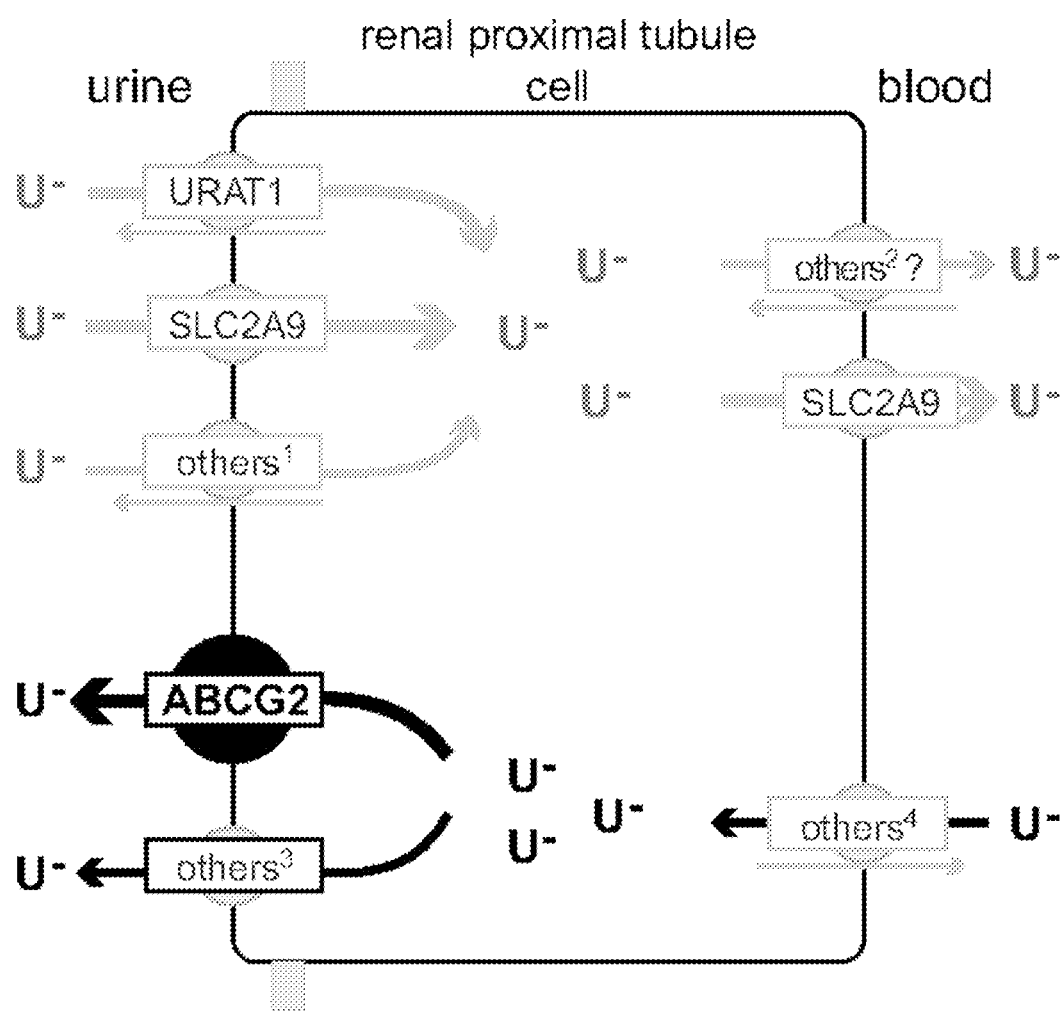
Figure 6:
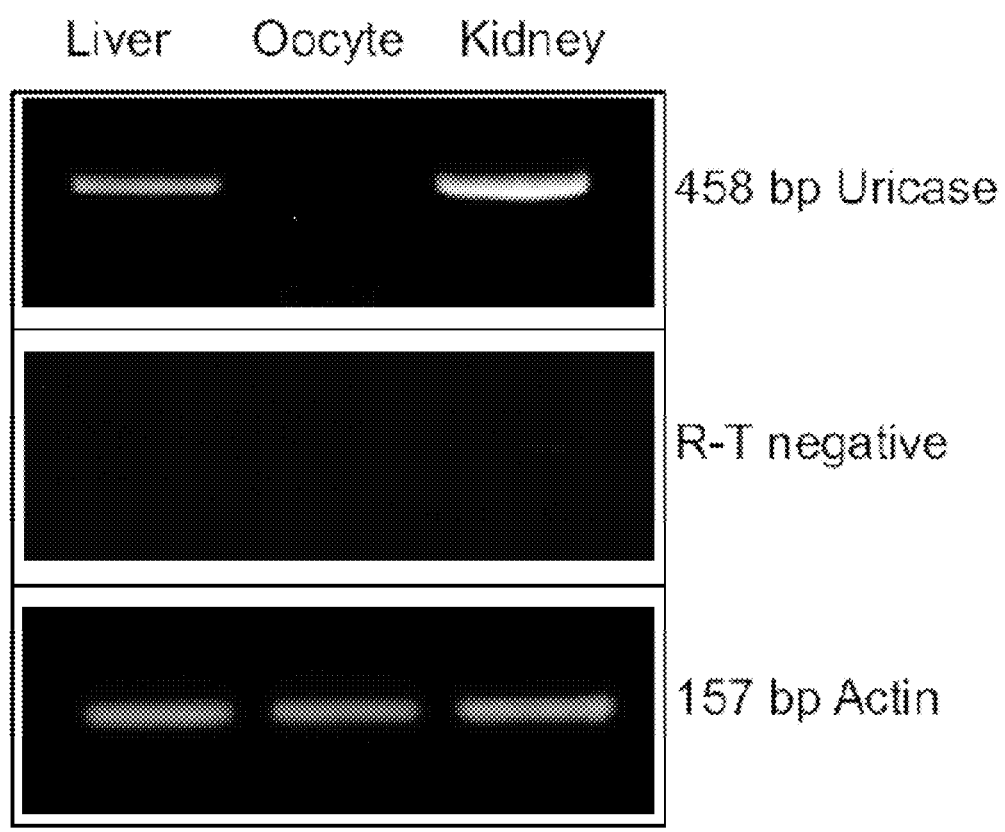

Having thus described the presently disclosed subject matter in general terms, reference will now be made to the accompanying Drawings, which are not necessarily drawn to scale, and wherein:

FIGS. 1A-1G show that ABCG2 is a urate transporter. (A) C-14 urate accumulation data from *Xenopus* oocytes injected with either $H_2O$ or mRNA coding for MRP4 or ABCG2. (B) Urate accumulation in oocytes injected with $H_2O$, ABCG2 WT mRNA (incubated with or without 5 µM FTC), or the nonfunctional ABCG2 mutant S187T (N=10 samples each and n=20 oocytes each for all accumulation experiments). (C) Urate accumulation is dependent on the extracellular urate concentration ($H_2O$ [circles]; S187T [squares]; WT [triangles]; N=10 and n=20 each). (D) Urate efflux in oocytes incubated overnight in 500 µM C-14 urate as relative efflux over time ($H_2O$ [circles]; ABCG2 [triangles]; N=5 and n=50 each). (E) Urate efflux depends on the intracellular urate concentration ($H_2O$ [circles]: slope=0.01, N=55; ABCG2 [triangles]: slope=0.03, N=55; P<0.001). (F) FTC (5 µM) inhibits urate export in native LLC-$PK_1$ renal proximal tubule cells as shown by increased urate accumulation in FTC-treated cells compared to non-treated control cells (N=6). (G) LLC-$PK_1$ cells express endogenous ABCG2 at the apical brush border membrane. Merged Z sections of LLC-$PK_1$ cells stained with BCRP1 antibody (upper segment) and nuclear DAPI stain (lower segment; scale bar, 5 µm). Mean±SEM; **P<0.001; *P<0.01;

FIGS. 2A-2D show that the ABCG2 Q141K mutation results in reduced urate transport. (A) Across-species comparison of the ABCG2 protein sequence. Sequence also is compared with the cystic fibrosis transmembrane conductance regulator (CFTR). Note the close proximity of Q141 in ABCG2 to the mutational hot spot F508 in CFTR. (B) Western blot of oocytes expressing ABCG2 WT or Q141K (monomers and dimers of ABCG2 are detected). Actin was used as a loading control. (C) Accumulation rates in oocytes expressing ABCG2 WT or Q141K normalized to ABCG2 expression level. (D) Efflux rates for ABCG2 WT and Q141K. (WT [triangles]: slope=0.01, N=55; Q141K [squares]: slope=0.02, N=55). Mean±SEM; **P<0.001;

FIG. 3 shows the surface expression of wild type and mutant ABCG2 in *Xenopus* oocytes. Biotinylation experiments reveal that the protein amounts and surface expression of the Q141K mutant are similar to those of the wild-type ABCG2 transporter. Actin was used as a loading control. The blot is representative of results from oocytes taken from two different female frogs;

FIGS. 4A-4D are an analysis of the ABCG2 locus and rs2231142 in population-based samples. (A) Association of urate levels and 602 SNPs in the ABCG2 region. Color legend: rs2231142 (blue), other SNPs coded by LD with rs2231142 based on HapMap CEU: red ($r^2$ with s2231142 0.8-1.0), orange ($r^2$=0.5-0.8), yellow ($r^2$=0.2-0.5), and white ($r^2$=0.2). Gene annotations are based on Build 36.1, and arrows correspond to direction of transcription and gene size. (B) Analyses as in A, conditional on genotype at rs2231142. (C) Mean serum urate levels by genotype at rs2231142 in white and black participants. *p-trend=$2*10^{-17}$, **p-trend=0.015. (D) Prevalence of gout by genotype at rs2231142. *p-trend=$4*10^{-6}$, **p-trend=0.04. Gout cases/overall sample in whites: GG (327/6792), GT (118/1601), TT (10/96); blacks: GG (187/2198), GT/TT (20/152);

FIG. 5 is a model of urate handling by human renal proximal tubule cells. The physiological relevance of urate transporters (named by their gene symbols) in humans is established by genetic variation causing hyper-/hypouricemia and gout for URAT1 (Enomoto A., et al., "Molecular identification of a renal urate anion exchanger that regulates blood urate levels," *Nature* 417:447-452 (2002)) and SLC2A9 (Dehghan A., et al., "Association of three genetic loci with uric acid concentration and risk of gout: a genome-wide association study," *Lancet* 372:1953-1961 (2008); Li S., et al., "The GLUT9 Gene Is Associated with Serum Uric Acid Levels in Sardinia and Chianti Cohorts," *PLoS Genet.* 3:e194 (2007); Wallace C., et al., "Genome-wide association study identifies genes for biomarkers of cardiovascular disease: serum urate and dyslipidemia," *Am. J. Hum. Genet.* 82:139-149 (2008); Doring A., et al., "SLC2A9 influences uric acid concentrations with pronounced sex-specific effects," *Nat. Genet.* 40:430-436 (2008); Vitart V., et al., "SLC2A9 is a newly identified urate transporter influencing serum urate concentration, urate excretion and gout," *Nat. Genet.* 40:437-442 (2008); and Matsuo H., et al., "Mutations in Glucose Transporter 9 Gene SLC2A9 Cause Renal Hypouricemia," *Am. J. Hum. Genet.* 83:744-751 (2008)). Transporters expressed in human kidney and shown to transport urate in model systems: OAT4 (Anzai N., et al., "New insights into renal transport of urate," *Curr. Opin. Rheumatol.* 19:151-157 (2007)); OAT1 (Yang Q., et al. "Genome-wide search for genes affecting serum uric acid levels: The Framingham Heart Study," *Metabolism* 54:1435-1441 (2005)); OAT3; MRP4 (Lawrence R. C., et al., "Estimates of the prevalence of arthritis and other rheumatic conditions in the United States, Part II," *Arthritis Rheum.* 58:26-35 (2008)); OAT1 (Dehghan A., et al., "Association of three genetic loci with uric acid concentration and risk of gout: a genome-wide association study," *Lancet* 372: 1953-1961 (2008)); OAT3 (Anzai N., et al., "New insights into renal transport of urate," *Curr. Opin. Rheumatol.* 19:151-157 (2007); Enomoto A., Endou H., "Roles of organic anion transporters (OATs) and a urate transporter (URAT1) in the pathophysiology of human disease," *Clin. Exp. Nephrol.* 9:195-205 (2005); and Rizwan A. N., Burckhardt G., "Organic anion transporters of the SLC22 family: biopharmaceutical, physiological, and pathological roles," *Pharm. Res.* 24:450-470 (2007)). Arrows indicate the direction of urate transport (gray, reabsorption; black, secretion). Abbreviations: U⁻: urate; and FIG. 6 is the expression of *Xenopus laevis* uricase mRNA in female *Xenopus* tissues. (Upper) RT-PCR of RNA extracted from kidney, liver, and oocytes. The upper 458-bp bands show the uricase RT-PCR product. (Middle) No uricase PCR product was detected in reactions performed with inactivated reverse transcriptase. (Lower) The 157-bp actin RT-PCR product as a positive control. Tissues from two frogs produced the same results.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

I. Modulation of ABCG2-Mediated Urate Transport to Treat Hyperuricemia and Gout

Gout is the most common inflammatory arthritis in men with a population prevalence of 1-3%, and increasing incidence; approximately three million individuals in the United States suffer from often insufficiently treated gout. Gout flares are extremely painful and can lead to debilitating joint destruction if left untreated. Gout is a consequence of elevated serum urate levels. Anzai et al., supra. Renal excretion of urate accounts for the majority of urate elimination from the body. Urate excretion in the kidney, however, is not completely understood. Prior to the present disclosure, the transporters mediating urate secretion in the human kidney had not been identified.

In some embodiments, the presently disclosed subject matter identifies a hitherto unknown urate efflux transporter, human ATP-binding cassette, sub-family G, 2 (ABCG2), which mediates renal urate secretion in humans. Further, the presently disclosed subject matter further shows that native ABCG2 locates to the brush border membrane of kidney proximal tubule cells. Activation of urate secretion through ABCG2 may decrease serum urate levels in patients having elevated serum urate levels. Therefore, ABCG2 constitutes an important drug target for hyperuricemia and gout. Thus, in some embodiments, the presently disclosed subject matter provides methods for enhancing transport of the wildtype ABCG2 protein, which is present in the majority of patients with gout.

In other embodiments, the presently disclosed subject matter identifies a common causal variant that accounts for more than 10% of gout in Caucasians. Introduction of the mutation Q141K encoded by the common SNP rs2231142, by site-directed mutagenesis resulted in 53% reduced urate transport rates compared to wildtype ABCG2 ($p<0.001$). Data from a population-based study of 14,783 individuals support rs2231142 as the causal variant in the region and show highly significant associations with urate levels (whites: $p=10^{-30}$, minor allele frequency (MAF) 0.11; blacks $p=10^{-4}$, MAF 0.03) and gout (adjusted odds ratio 1.68 per risk allele, both races).

Thus, in some embodiments, the presently disclosed subject matter provides methods for enhancing transport of ABCG2 Q141K, the causal loss of function mutation disclosed immediately hereinabove. Preliminary data indicate that the transport defect of ABCG2 Q141K is caused, in part, by degradation of misfolded protein. This mechanism is similar to the mechanism reported for CFTR ΔF508, the most common mutation found in Cystic Fibrosis patients. ABCG2 and CFTR belong to the family of ABC transporters. The mutations in both genes affect the nucleotide-binding domains of the proteins and the mutated residues in both proteins are immediate neighbors at the amino acid level when the sequences are aligned. Correctors of CFTR folding have been developed and have been shown to improve CFTR ΔF508 processing and transport function. See Loo T. W., et al., "The chemical chaperone CFcor-325 repairs folding defects in the transmembrane domains of CFTR-processing mutants," *Biochem J.* 395(3):537-42 (2006); Van Goor F. et al., "Rescue of DeltaF508-CFTR trafficking and gating in human cystic fibrosis airway primary cultures by small molecules," *Am. J. Physiol. Lung Cell Mol. Physiol.* 290(6): L1117-30 (2006). Based on the similarity of the defect in CFTR and ABCG2, the correctors of folding developed for CFTR also may improve ABCG2 processing and transport function. Preliminary experiments show that the expression level of mutant ABCG2 can be increased pharmacologically.

In yet other embodiments, based on the observation that ABCG2 mediates urate secretion in the kidney, the presently disclosed subject matter provides a screen for activators of ABCG2. Accordingly, the presently disclosed high-throughput screens for activators of ABCG2 can be used to identify lead compounds for the development of novel drugs to treat hyperuricemia and gout. More particularly, a high throughput screen using transport of fluorescently labeled substrates for ABCG2 can be used to screen for activators. Subsequently, hits from this high-throughput screen can be evaluated using radio-labeled urate in transport assays. The presently disclosed screen for activators uses several approaches including, but not limited to, (a) chemical libraries; and (b) cellular signaling pathways that have be shown to modulate other renal transporters including, but not limited to, second messengers, kinases, phosphases, and receptors.

In summary, pharmacological activation of wild type and mutant ABCG2 is proposed as a mechanism to increase renal urate elimination. Most likely, different drugs will be required to enhance either wildtype or mutant ABCG2 transport function. The use of a diagnostic SNP chip is proposed to allow for differential therapeutic approaches depending on genotype.

A. ABCG2 is a Urate Transporter

To investigate whether ABCG2 is a hitherto unknown urate transporter, human ABCG2 was expressed in *Xenopus* oocytes. Accumulation of radiolabeled urate in oocytes and urate efflux rates from oocytes were measured. Urate accumulation was significantly decreased by 75.5% in oocytes expressing ABCG2 compared with water-injected control oocytes. See FIG. 1A. Further, ABCG2-expressing oocytes showed lower urate concentrations than oocytes expressing the known urate efflux transporter MRP4. See Van Aubel R. A., et al., "Human organic anion transporter MRP4 (ABCC4) is an efflux pump for the purine end metabolite urate with multiple allosteric substrate binding sites," *Am. J. Physiol. Renal. Physiol.* 288:F327-333 (2005).

Figure 1:
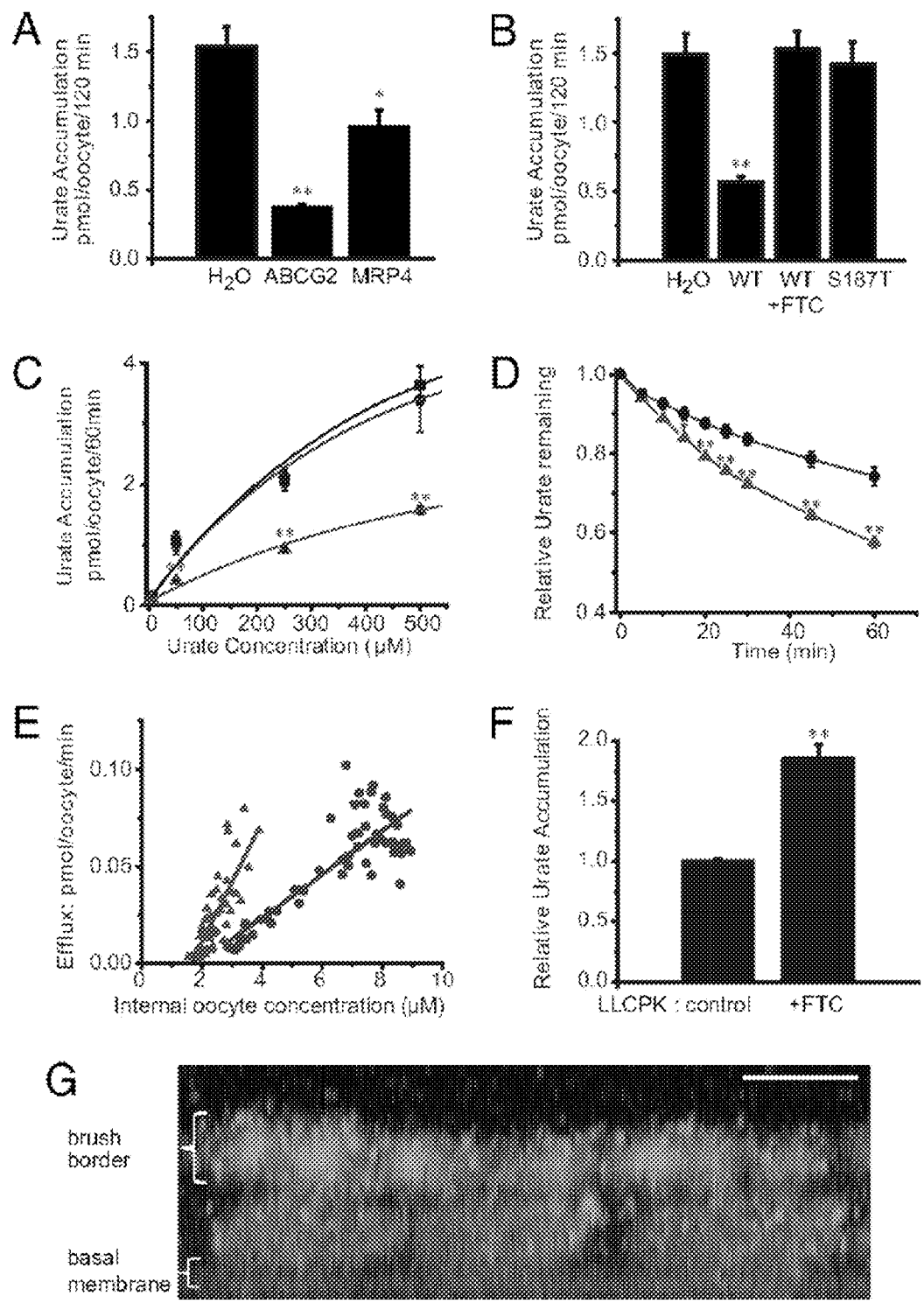
Figure 2:
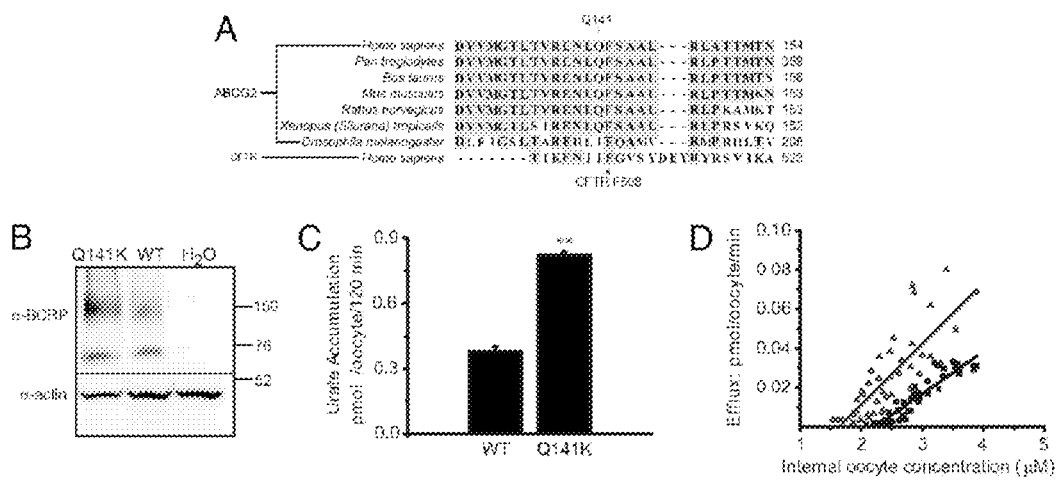

Referring now to FIG. 1B, the reduced urate accumulation in ABCG2-expressing oocytes was absent in the presence of fumitremorgin C (FTC), a specific ABCG2 inhibitor, or after introduction of a mutation in ABCG2 (187T) that is known to disrupt transport of chemotherapeutic agents. See Doyle L. A., et al., "A multidrug resistance transporter from human MCF-7 breast cancer cells," *Proc. Natl. Acad. Sci. USA* 95:15665-15670 (1998); Polgar O., Robey R. W., Bates S. E., "ABCG2: structure, function and role in drug Response," *Expert Opin. Drug Metab. Toxicol.* 4:1-15 (2008).

ABCG2-expressing oocytes showed significantly lower urate accumulation over a wide range of extracellular concentrations compared with control cells or cells expressing the loss-of-function mutation ABCG2 187T. See FIG. 1C. The reduced urate accumulation was due to ABCG2-mediated export of urate out of the cells as shown in experiments monitoring the decrease of the intracellular urate concentration over time in oocytes preloaded with radiolabeled urate. See FIG. 1D. Further, ABCG2-mediated urate efflux was dependent on the intracellular urate concentration and significantly higher in ABCG2-expressing oocytes than in control oocytes. See FIG. 1E. Together, these data show that ABCG2 is a urate efflux transporter.

B. ABCG2 in Renal Epithelial Cells

In mammals, the proximal tubule is the major site of renal urate handling. See Anzai et al., "New insights into renal transport of urate," *Curr. Opin. Rheumatol.* 19:151-157 (2007). To study the urate transport capacity of endogenous ABCG2 in polarized renal epithelial cells, the urate accumulation in native LLC-$PK_1$ cells was measured. Inhibition of ABCG2 by FTC resulted in a significant impairment of urate export as shown by significantly higher intracellular urate accumulation compared with control cells. See FIG. 1F. To investigate whether ABCG2 mediates renal reabsorption or secretion of urate, its subcellular localization was examined. In polarized LLC-$PK_1$ cells, ABCG2 was localized to the apical brush border membrane, see FIG. 1G, which is consistent with the recent demonstration of ABCG2 in the brush border of human proximal tubule cells. See Huls M., et al., "The breast cancer resistance protein transporter ABCG2 is expressed in the human kidney proximal tubule apical membrane," *Kidney Int* 73:220-225 (2008). The presently disclosed subject matter therefore establishes that ABCG2 is a secretory urate transporter in the proximal tubule. Consequently, mutations in ABCG2 that increase serum urate concentrations must be loss-of-function mutations.

C. Impaired Urate Transport of ABCG2 Q141K

The most significant SNP in a genome-wide association study (GWAS) of serum urate levels was the non-synonymous coding SNP rs2231142 in exon 5 of ABCG2. See Dehghan A., et al., "Association of three genetic loci with uric acid concentration and risk of gout: a genome-wide association study," *Lancet* 372:1953-1961 (2008). The glutamine (Q) residue at ABCG2 position 141, encoded by the rs2231142 G allele, is highly conserved across species. See FIG. 2A. Interestingly, Q141 is located in the nucleotide-binding domain of ABCG2 right next to the corresponding amino acid F508 in the nucleotide-binding domain of CFTR, a residue commonly mutated in patients with cystic fibrosis. To test whether this SNP is not only statistically associated, but causally related to elevated urate levels, the mutation Q141K encoded by the rs2231142 T allele was introduced by site-directed mutagenesis. Wild-type and Q141K mutant ABCG2 showed similar expression levels at the cell surface when expressed in *Xenopus* oocytes. See FIG. 3. Notably, Q141K-expressing oocytes showed 54% reduced urate transport rates compared with those expressing wild-type ABCG2 at similar levels, see FIGS. 2B and 2C, and decreased urate efflux across a range of intracellular urate concentrations. See FIG. 2D. Evidence for Q141K as a causal loss-of-function variant is supported by data showing reduced transport of chemotherapeutic agents by this mutation. See Polgar O., Robey R. W., Bates S. E., "ABCG2: structure, function and role in drug Response," *Expert Opin. Drug Metab. Toxicol.* 4:1-15 (2008).

D. Relevance in the General Population

To investigate the genomic context and to quantify the effect of this common causal variant in the general population, 10,902 self-reported white and 3,881 black participants of the Atherosclerosis Risk in Communities (ARIC) Study, see The ARIC investigators, "The Atherosclerosis Risk in Communities (ARIC) Study: Design and objectives," *Am. J. Epidemiol.* 129:687-702 (1989), who had serum urate measured and self-reported information on gout were investigated. Information on the SNP rs2231442, encoding the Q141K variant, was available as an imputed SNP from genome-wide Affymetrix 6.0 data along with 601 other SNPs in a 600-kb region containing ABCG2, and also genotyped directly using the TaqMan assay.

Figure 4:
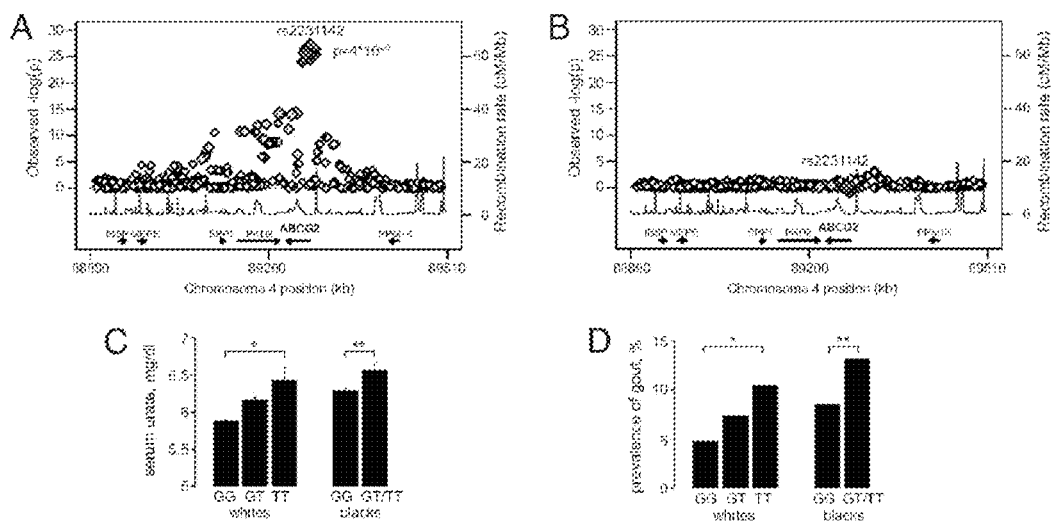

In a subset of 8,092 white participants with available GWAS data, the rs2231142 T allele showed highly significant association with higher urate levels in multivariable adjusted association analyses ($P=4\times10^{-27}$; see FIG. 4A). Other strongly associated SNPs were located in introns or downstream of ABCG2 and were in perfect or high linkage disequilibrium with rs2231142. After repeating the analyses conditional on genotype at rs2231142, no significant associations in the region remained, see FIG. 4B, which supports the presence of a single common causal variant in the region.

In both white and black study participants, serum urate levels showed a graded and significant increase across genotypes at the directly genotyped rs2231142 variant. See FIG. 4C. The association became more significant when adjusting for known correlates of serum urate levels: age, sex, BMI, alcohol consumption, and antihypertensive medication intake (P trend=$3\times10^{-30}$ for whites and $P=7\times10^{-4}$ for blacks). Adjustment for sex explained the largest part of this difference, with the genetic effect in men significantly stronger than in women, see Dehghan A., et al., "Association of three genetic loci with uric acid concentration and risk of gout: a genome-wide association study," *Lancet* 372:1953-1961 (2008), which is in agreement with higher rates of renal ABCG2 expression in men compared with women. See Krishnamurthy P., Schuetz J. D., "Role of ABCG2/BCRP in biology and medicine," *Annu. Rev. Pharmacol. Toxicol.* 46:381-410 (2006).

Similarly, the prevalence of gout was significantly different across genotypes in both whites and blacks. See FIG. 4D. Of note, the prevalence of gout was 40% among black TT carriers, but genotypes GT and TT were pooled because of the low minor allele frequency of 3% in blacks. The multivariable-adjusted relative odds of gout per each copy of the T allele were 1.68 in both races ($P=2\times10^{-7}$ in whites and $P=0.05$ in blacks); the consistency of the effect size in groups of different ancestry further supports causality of rs2231142. In this context, it is of interest that the T allele frequency at rs2231142 among Asian populations (HapMap CHB, and JPT) is approximately 30% compared with 11% in white ARIC participants, and gout prevalence in U.S. individuals of Asian ancestry is about three times higher compared with individuals of European ancestry. See Krishnan E., Lienesch D., Kwoh C. K., "Gout in ambulatory care settings in the United States," *J. Rheumatol.* 35:498-501 (2008). Among the white study participants, population-attributable risk calculations yielded that a conservatively estimated 10% of gout cases could be attributed to the Q141K mutation.

The presently disclosed findings are of substantial clinical interest because of the high prevalence of the Q141K mutation in individuals of European and Asian ancestry and the substantial population attributable risk. Gout has a high prevalence of approximately 3 million affected individuals in the U.S.; the treatment is often insufficient, with only 21% of gout patients who receive the most common urate-lowering treatment, reaching optimal serum urate levels in clinical trials. See Becker M. A., et al "Febuxostat compared with allopurinol in patients with hyperuricemia and gout," *N. Engl. J. Med.* 353:2450-2461 (2005); Schumacher H. R., Jr., et al., "Effects of febuxostat versus allopurinol and placebo in reducing serum urate in subjects with hyperuricemia and gout: A 28-week, phase III, randomized, double-blind, parallel-group trial" *Arthritis Rheum.* 59:1540-1548 (2008). ABCG2 therefore represents an important drug target.

Referring now to FIG. 5, a summary and integration of the presently disclosed subject matter is provided. Based on the urate efflux capacity of ABCG2, its apical cellular localization, and the identification of a loss-of-function mutation that causes increased serum urate levels and gout, without wishing to be bound to any one particular theory, ABCG2 is thought to be a secretory urate transporter in the proximal renal tubule. The physiological importance of ABCG2 in humans is illustrated by the sizable differences in serum urate levels and the prevalence of gout caused by genetic variation in ABCG2.

E. Conclusion

In summary, the presently disclosed subject matter overcomes key limitations of GWAS, namely establishing gene function and determining causality of an associated genetic variant. See Donnelly P., "Progress and challenges in genome-wide association studies in Humans," *Nature* 456: 728-731 (2008); McCarthy M. I., et al., "Genome-wide association studies for complex traits: Consensus, uncertainty and challenges," *Nat. Rev. Genet.* 9:356-369 (2008). More particularly, the presently disclosed subject matter shows that ABCG2 is a urate efflux transporter and rs2231142 (Q141K) represents a loss-of-function mutation that causes hyperuricemia and gout. This information completes the chain of evidence from association to causation and supports the common disease-common variant hypothesis in the etiology of gout.

II. Activators of ABCG2

As used herein, the term "activator" refers to any molecule that activates, enhances, increases, and/or improves the activity of an ABCG2 transporter. Activity may include, but is not limited to, excretion, transport, or clearance of a substrate (e.g. urate and D-luciferin) by ABCG2. In one embodiment, an activator improves the activity of the native or wildtype ABCG2 transporter. In another embodiment, an activator improves the activity of a mutant ABCG2 transporter (for example, the rs2231142 (Q141K) mutant) to a level close to, equal to, or greater than the activity of wildtype ABCG2 transporter. As used herein, the term "candidate substance" or "candidate agent" refers to any molecule that may potentially activate, enhance, increase, and/or improve the activity of the ABCG2 transporter. The candidate substance may be a protein or fragment thereof, a small molecule, or even a nucleic acid molecule. It may prove to be the case that the most useful pharmacological compounds will be compounds that are structurally related to the known correctors of CFTR folding. Using lead compounds to help develop improved compounds is known as "rational drug design" and includes not only comparisons with known activators, but also predictions relating to the structure of target molecules.

Generally, the goal of rational drug design is to produce structural analogs or derivatives of biologically active polypeptides or target compounds. As used herein, an "analog" refers to a chemical compound in which one or more individual atoms or functional groups of a parent compound have been replaced, either with a different atom or with a different functional group. For example, thiophene is an analog of furan, in which the oxygen atom of the five-membered ring is replaced by a sulfur atom. As used herein, a "derivative" refers to a chemical compound which is derived from or obtained from a parent compound and contains essential elements of the parent compound but typically has one or more different functional groups. Such functional groups can be added to a parent compound, for example, to improve the molecule's solubility, absorption, biological half life, and the like, or to decrease the toxicity of the molecule, eliminate or attenuate any undesirable side effect of the molecule, and the like. An example of a derivative is an ester or amide of a parent compound having a carboxylic acid functional group.

By creating such analogs or derivatives, it is possible to fashion drugs, which are more active or stable than the natural molecules, which have different susceptibility to alteration or which may affect the function of various other molecules. In one approach, one would generate a three-dimensional structure for a target molecule, or a fragment thereof. This three-dimensional structure could be accomplished by x-ray crystallography, computer modeling or by a combination of both approaches.

It also is possible to use antibodies to ascertain the structure of a target compound activator. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore.

On the other hand, one may simply acquire, from various commercial sources, small molecule libraries that are believed to meet the basic criteria for useful drugs in an effort to identify useful compounds. Screening of such libraries, including combinatorially generated libraries (e.g., peptide libraries or small molecule chemical libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate agents may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened also could be derived or synthesized from chemical compositions or man-made compounds. Thus, it is understood that the candidate substance identified using the methods of the present invention may be a peptide, polypeptide, polynucleotide, small molecule or any other compound that may be designed through rational drug design starting from known compounds.

In addition to the activating compounds initially identified, the inventors also contemplate that other sterically similar compounds may be formulated to mimic the key portions of the structure of the activators. Such compounds, which may include peptidomimetics of peptide activators, may be used in the same manner as the initial activators.

Regardless of the type of ABCG2 activator identified by the present screening methods, the effect of the activation by such a compound results in a difference as compared to that observed in the absence of the added candidate substance.

III. Methods of Screening for Activators of the ABCG2 Transporter.

A. Screening for ABCG2 Activators

The present invention provides methods for identifying activators of the function of the ABCG2 transporter. These methods may comprise random screening of large libraries of candidate substances. Alternatively, the methods may be used to focus on a particular class or classes of compounds selected with an eye toward structural attributes that are believed to make them more likely to activate the function of ABCG2. For example, as described herein, the correctors of folding developed for CFTR also may improve ABCG2 processing and transport function.

To identify an ABCG2 transporter activator, one generally will determine the function of the ABCG2 transporter in the presence and absence of the candidate agent. For example, a method generally comprises: a) providing a candidate agent; b) contacting the candidate agent with a cell expressing ABCG2, or a cell extract or cell membrane preparation that comprises the ABCG2 transporter, or a suitable experimental animal; c) measuring one or more characteristics of the ABCG2 transporter, cell, cell extract or cell membrane preparation, or animal, that reflects the function or activity of the ABCG2 transporter; and d) comparing the characteristic measured in step (c) with the characteristic of the ABCG2 transporter, cell, cell extract or cell membrane preparation, or animal in the absence of the candidate agent, wherein a difference between the measured characteristics indicates that the candidate agent is, indeed, an activator of the ABCG2 transporter. Comparing the characteristic measured as described in the steps above includes measurement of excretion, transport or clearance of an ABCG2 substrate, including urate and D-luciferin.

Assays may be conducted in cell-free systems, such as cellular extracts, cell membrane preparations which may be prepared by lysing cells, in isolated cells, in cells that express endogenous ABCG2 transporter, in cells that are genetically engineered to express ABCG2 transporter, in cells that exogenously or endogenously express mutant or functionally deficient ABCG2 transporters, or in organisms including transgenic animals or animal models of diseases wherein the disease is associated with the ABCG2 transporters. Thus, knockouts for the ABCG2 transporter may be used (Giros et al., 1996; Sora et al., 2001). It will, of course, be understood that all the screening methods of the present invention are useful in themselves notwithstanding the fact that effective candidates may not be found. The invention provides methods for screening for such candidates, not solely methods of finding them.

B. Automation

The inventors further contemplate that all methods disclosed herein are adaptable to high-throughput formats using robotic fluid dispensers, multi-well formats and fluorescent plate readers for the identification of ABCG2 activators.

C. In Vitro Assays

A quick, inexpensive and simple assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces, such as dipsticks or beads.

One example of a cell-free assay in this invention is the use of cellular extracts that comprise ABCG2; these may be cell membrane preparations that comprise the ABCG2 transporter.

Another example is a cell-binding assay. While not directly addressing function, the ability of a candidate agent to bind to a target molecule (in this case the ABCG2 transporter) in a specific fashion is strong evidence of a related biological effect. For example, binding of a molecule to the ABCG2 transporter may be indicative of a modulatory effect. For example, binding of a molecule may, in and of itself, be inhibitory, due to steric, allosteric or charge-charge interactions. The ABCG2 transporter protein may be either free in solution, fixed to a support, expressed in or on the surface of a cell. Either the ABCG2 transporter or the candidate agent may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

D. In Cyto Assays

The present invention also contemplates the screening of agents for their ability to activate the ABCG2 transporter in cells. Various cells and cell lines can be utilized for such screening assays as long as the cell expresses the ABCG2 transporter. This includes cells specifically engineered to expresses the ABCG2 transporter.

E. In Vivo Assays

In vivo assays involve the use of various animal models, including transgenic animals that have been engineered to have specific defects, or carry markers that can be used to measure the ability of a candidate agent to reach and affect the activity of the ABCG2 transporter in different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for activators may be conducted using an animal model derived from any of these species.

In such assays, one or more candidate agents are administered to an animal, and the ability of the candidate agent(s) to alter one or more characteristics that are a result of ABCG2 function or activity, as compared to a similar animal not treated with the candidate agent(s), identifies an activator. The characteristics may be any of those discussed herein with regard to the function of ABCG2 and its downstream effects on hyperuricemia and gout.

Furthermore, in specific embodiments, the present invention is directed to a method for determining the ability of a candidate agent to activate ABCG2, generally including the steps of: administering a candidate substance to the animal; and determining the ability of the candidate substance to change one or more characteristics of the ABCG2 transporter.

Methods for in vivo imaging are described in Herrera & Banner (1990), and in Herrera et al. (1990), (both incorporated herein by reference). In situ methods for analysis are described in Pietruck & Ullrich (1995) and Rohlicek & Ullrich (1994), (also incorporated herein by reference). These methods may be suitably modified with the other teachings of this specification to perform the in vivo assays described herein.

Treatment of these animals with candidate agents will involve the administration of the agent, in an appropriate form, to the animal. Administration will be by any route that could be utilized for clinical or non-clinical purposes, including but not limited to oral, nasal, buccal, or even topical. Alternatively, administration may be by parenteral methods such as intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in vitro or in cyto assays.

F. Vectors for Delivery and Expression of ABCG2

Within certain embodiments, expression vectors are employed to express the ABCG2 transporter in a cell. The specification provides a description of transformation of HEK cells to express exogenous ABCG2. Furthermore, U.S. Pat. Nos. 5,312,734, 5,418,162, and 5,424,185, each incorporated herein by reference, describe nucleic acids, vectors, and host cells used to express various proteins in cells. As will be understood by one of skill in the art, the present invention is not limited to any particular type of expression vectors and expression vectors encoding the ABCG2 transporter can be used in any cell type. Additionally, as set forth above one may also use mutant versions, isoforms, and other variants of the ABCG2 transporter in the methods of the invention.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products also are provided, as is an element that links expression of the drug selection markers to expression of the polypeptide. Gene transfer may rely on viral elements as in the case of viral vectors, or non-viral means including lipids (liposomes, nanoparticles), electroporation, and the like.

G. Illustrative Screening Method

In particular embodiments, the screening methods of the present invention may comprise a D-luciferin based bioluminescence imaging assay. D-luciferin, the substrate of firefly luciferase (fLuc), is a specific substrate for ABCG2. Zhang et al., *Cancer Res.* 67:9389-97 (2007). fLuc is the most commonly used reported for imaging transgene expression in vivo. fLuc catalyzes the oxidation of D-luciferin, releasing photons that can be quantified through bioluminescence imaging (BLI). See Rettig et al., *Analytic Biochem.* 355:90-4 (2006). BLI is an increasingly widespread imaging technique, provides an extremely high signal-to-background (S/B) ratio, and is easy to perform. See Brovko et al., *Sci. Prog.* 90:129-60 (2007).

In cells that express both ABCG2 and fLuc, a baseline of photonic output can be established using wildtype ABCG2. Photonic output through catalyzation of D-luciferin can further be determined for cells that express the mutant ABCG2, rs2231142 (Q141K) and fLuc. Similar measurements can be determined for cells that express other known mutants of the ABCG2 transporter. Moreover, in certain embodiments, the effect of candidate agents on bioluminescence in such cell lines (wildtype ABCG2, mutant ABCG2 such as rs2231142 (Q141K), etc.) can be determined in high throughput fashion to identify activators of ABCG2.

In several embodiments, the methods of the present invention may utilize the ABCG2-overexpressing HEK293 cell line stably transfected with CMV-luc2CP/Hygro (also referred to as HEK293/ABCG2/fLuc). See Zhang et al., *Neoplasia* 11:96-101 (2009); Zhang et al., *Cancer Res.* 69(14): 5867-75 (2009). Control empty vector-transfected HEK293 cells may be stably transfected with CMV-luc2CP/Hygro in the same way and may be referred to as HEK293/empty/fLuc. The cells may be cultured in an appropriate medium including MEM (Invitrogen) supplemented with 10% fetal bovine serum (FBS), penicillin, and streptomycin; medium containing 1 mg/ml G418 and 100 µg/ml hygromycin B; or RPMI 1640 supplemented with 10% FBS, penicillin, and streptomycin. All cultures may be maintained at 37° C. in a humidified 5% $CO_2$/95% air incubator.

In particular screening methods utilizing the BLI assay, HEK293/ABCG2/fLuc cells are plated into 96-well plates at a density of $4 \times 10^4$/100 µL per well and allowed to attach overnight. The following day, 10 µL of each candidate agent or the control solvent is transferred from a compound library in a 96-well, high-throughput format into the wells using a multichannel pipette. The final concentration of each candidate agent is determined. D-luciferin (5 µL; 1.2 mg/mL in PBS) is then added to achieve a final concentration of about 50 µg/mL. The plates are gently tapped to assure that all solutions are well mixed, and imaging commences immediately. Images may be taken every 5 minutes for about 1 hour. Light output from each well is quantified at the 40-min. time point after initiation of imaging, and the S/B ratio of the light output from each candidate agent divided by that from the control well is calculated. This S/B ratio serves as an indicator of the potency of the ABCG2 activation (or inhibition), the mechanism by which BLI signal is decreased (or enhanced).

Signal-to-noise ratio (S/B) and Z' values, which indicate the robustness of the assay, are calculated using methods known in the art. See Zhang et al., *J. Biomol. Screen* 4:67-73 (1999). Background is defined as the light output from cells incubated with D-luciferin and the solvent only.

In certain embodiments, the screening methods of the present invention may utilize in vivo BLI. For example, HEK293/ABCG2/fLuc and HEK293/empty/ABCG2 cells are implanted s.c. into 6-wk-old female nude mice at $1 \times 10^6$ at each site. The IVIS 200 small animal imaging system (Xenogen Corp.) is used for BLI and 2.5% isoflurane is used for anesthesia. D-luciferin is injected i.p. into mice at 150 mg/kg, and imaging is performed every few minutes for about 1 hour. ABCG2 candidate agent is administered via tail vein injection as a bolus during imaging, with imaging continued thereafter.

With regard to data analysis, Living Image (Xenogen) and IGOR (Wavemetrics) image analysis software is used to superimpose and analyze the corresponding grayscale photographs and false color BLI images. Light intensities of regions of interest are expressed as total flux (photons/second). The IC50 values of identified ABCG2 activators are calculated using GraphPad Prism version 4.0 for Windows (GraphPad Software) using variable-slope logistic nonlinear regression analysis. Data is presented as mean±SE (n=3).

The sensitivity of the BLI assay may be further evaluated by searching libraries for previously known ABCG2 activators, including known correctors of CFTR folding.

The candidate agents may also be tested utilizing the system described in Example 1 below in which candidate agents are screened for their effect on urate transport in *Xenopus* oocytes. Moreover, candidate agents may be further evaluated and confirmed using established assays known to those of ordinary skill in the art.

IV. Assessing Risk of Subject to Hyperuricmia and/or Gout Based on Presence of Absence of the ABCG2 SNP rs2231442

The present invention further relates to methods that identify the presence of the ABCG2 single nucleotide polymorphism (SNP) rs2231442 in a subject and correlating the presence of such SNP to a subject's risk of developing gout and/or hyperuricemia. As used herein, the term "risk" refers to a predictive process in which the probability of a particular outcome, e.g., a likelihood of a subject developing gout and/ or hyperuricemia, is assessed.

Any sample comprising cells or nucleic acids from the patient or subject to be tested may be used. Preferred samples are those easily obtained from the patient or subject. Such samples include, but are not limited to, blood, serum, plasma, urine, saliva, epithelial cell swabs, synovial fluid, or other body fluid or tissue obtained from an individual. It will be appreciated that the test sample may comprise the ABCG2 nucleic acid that has been amplified using any convenient technique, e.g., PCR, before analysis. Any available means of detecting a sequence polymorphism(s) of the present invention may be used in the methods.

Any analytical procedure may be used to detect the presence or absence of the rs2231442 variant. In general, the detection of allelic variation requires a mutation discrimination technique, optionally an amplification reaction and optionally a signal generation system. Many current methods for the detection of allelic variation are reviewed by Nollau et al., *Clin. Chem.* 43:1114-1120 (1997); and in standard textbooks, for example, Laboratory Protocols for Mutation Detection by U. Landegren, Oxford University Press, 1996 and PCR, 2nd Edition by Newton & Graham, BIOS Scientific Publishers Limited, 1997.

Any means of mutation detection or discrimination may be used. For instance DNA sequencing, scanning methods, hybridization, extension-based methods, incorporation-based methods, restriction enzyme-based methods and ligation-based methods may be used in the methods of the invention. Sequencing methods include, but are not limited to, direct sequencing and sequencing by hybridization. Scanning-methods include, but are not limited to, protein truncation test (PTT), single-strand conformation polymorphism analysis (SSCP), denaturing gradient gel electrophoresis (DGGE), temperature gradient gel electrophoresis (TGGE), cleavase, heteroduplex analysis, chemical mismatch cleavage (CMC), and enzymatic mismatch cleavage.

Hybridization-based methods of detection include, but are not limited to, solid phase hybridization such as dot blots, multiple allele specific diagnostic assay (MASDA), reverse dot blots, and oligonucleotide arrays (DNA Chips). Solution phase hybridization amplification methods may also be used, such as Taqman®.

Extension based methods include, but are not limited to, amplification refractory mutation system (ARMS), amplification refractory mutation system linear extension (ALEX), and competitive oligonucleotide priming system (COPS).

Incorporation-based detection methods include, but are not limited to, mini-sequencing and arrayed primer extension (APEX). Restriction enzyme-based detection systems include, but are not limited to, RFLP, and restriction site generating PCR. Lastly, ligation based detection methods include, but are not limited to, oligonucleotide ligation assay (OLA).

Signal generation or detection systems that may be used in the methods of the invention include, but are not limited to, fluorescence methods, such as fluorescence resonance energy transfer (FRET), fluorescence quenching, fluorescence polarization, as well as other chemiluminescence, electrochemiluminescence, Raman, radioactivity, calorimetric methods, hybridization protection assay and mass spectrometry.

Further amplification methods include, but are not limited to, self sustained replication (SSR), nucleic acid sequence based amplification (NASBA), ligase chain reaction (LCR), strand displacement amplification (SDA) and branched DNA (b-DNA).

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Functional Studies

*Xenopus laevis* Oocytes

Oocytes were removed from female pigmented *Xenopus laevis* (*Xenopus* 1 Inc.) and de-folliculated using collagenase A (Roche) in $Ca^{2+}$-free OR-2 ringer solution. Stage V-VI oocytes were selected and injected (Nanoinject II, Drummond Scientific) with 50 nL of either mRNA or $H_2O$ (as a control). All experiments were performed on the fourth day after injection. Oocytes after injection were cultured in a modified L-15 media (OR-3) and kept at 15-20° C. mRNA was prepared using the SP6 mMessage mMachine (Ambion Inc.) according to the manufactures protocol. The Q141K mutant was created using site directed mutagenesis with the primers: 5'-GGT GAG AGA AAA CTT AAA GTT CTC AGC AGC TC 3-' (SEQ ID NO. 1) and 5'-GAG CTG CTG AGA ACT TTA AGT TTT CTC TCA CC-3' (SEQ ID NO. 2) and completed using the Quick-Change Lightning kit (Stratagene) according to the manufacturer's protocol.

C-14 Uric Acid

Radiolabeled C-14 uric acid (American Radio-labeled Chemicals) was dissolved in a stock solution of 2 mM NaOH with a final urate concentration of 2 mM (either 2 mM hot-radio labeled urate or 1 mM hot and 1 mM cold urate). For oocyte transport experiments, the radio labeled C-14 urate was included at various concentrations in ND96 ringers solution (in mM: 96 NaCl, 2 KCl, 2 $MgCl_2$, 5 Hepes, 1.8 CaCl2, pH 7.5, and 5 mM glucose for overnight incubation experiments).

Oocyte Transport Experiments

For accumulation studies, oocytes were incubated either for 1 or 2 h at room temperature in 50 μM C-14 urate or overnight in 500 μM C-14 urate at 15° C. After incubation the oocytes were washed in ice-cold ND96 solution 3-5 times to remove any superficial, residual C-14 urate from the oocytes. Oocytes were then pooled for scintillation counting. For the 1-2-h accumulation studies, after incubation in the C-14 urate solution, two oocytes were placed in each scintillation tube (N) with lysis buffer of 1 N NaOH; a total of 20 oocytes (n) was used for each treatment. For the overnight accumulation studies, after incubation, 10 oocytes were pooled into one scintillation vial (N) with the lysis buffer; a total of 50 oocytes (n) was used for each treatment.

For the efflux studies, 50 oocytes expressing each of the different proteins of interest were incubated overnight in 500 μM C-14 urate at 15-20° C., washed 5 times in ice cold ND96 solution, and then, in groups of 10, placed into a well with 500 μL room temp ND96. After 5 min, the bath was collected and replaced with a new bath solution. Bath collections continued for 2-3 h. After the final collection, the oocytes also were collected and placed into scintillation vials (10 per vial) containing 1N NaOH lysis buffer. All samples in scintillation vials were mixed with 5-mL scintillation fluid and their cpm determined using a scintillation counter (LS600 LL, Beckman Coulter Inc.). To confirm that after 24 h the accumulated intracellular urate had not been metabolized by the uricase enzyme, oocytes, as well as other tissues, were probed for the presence of uricase mRNA using RT-PCR. See FIG. 6. Total RNA was extracted from *Xenopus laevis* oocytes, kidneys, and liver using the Qiagen RNeasy Mini Kit (Qiagen Inc.) according to the manufacturer's protocol. Thirty de-folliculated oocytes were pooled for the RNA preparation. For both reverse transcriptase and PCR, the Qiagen One Step RTPCR kit (Qiagen Inc.) was used according to the manufacturer's protocol. The reaction mixtures were run for 35 cycles. As a control for genomic DNA contamination, the One Step enzyme mixture (containing the reverse transcriptase) was added only after the mixtures reached 94° C., inactivating the reverse transcriptase. The following primers were used for the detection of uricase RNA: 5'-ACC ATC TAT GCC TTG ACT AAA CTC-3' (SEQ ID NO. 3) and 5'-TAA GGA CCA GCA AAT GTA TCA AG-3' (SEQ ID NO. 4). For the actin 5 control, 5'-CTGAGTTCATGAAGGATCAC-3' (SEQ ID NO. 5) and 5'-AAA TTT ACA GGT GTA CCT GC-3' (SEQ ID NO. 6) was used.

For each batch of counting, a set of control vials of known volume and concentration of C-14 urate was included. Based on the counts measured in any of the experimental samples and assuming that stage V and VI oocytes have an approximate average volume of 1 μL (16), the use of control vials allowed for the calculation of intracellular C-14 urate concentrations. Statistical comparisons were performed using non-paired Student t-tests and linear regression analyses. Exponential and linear fits were performed using Origin 8 software (OriginLab Corp.).

LLC-PK$_1$ Experiments

LLC-PK$_1$ porcine renal epithelial cells were cultured in Dulbecco's Modified Eagle medium (DMEM) supplemented with 10% FBS. LLC-PK$_1$ cells were seeded at a high density into a 6-well plate and accumulation experiments were performed after the cells polarized. The cells were incubated in DMEM containing 500 µM cold urate and 25 µM hot urate with or without 5 µM FTC (US Biologicals); the incubation lasted 120 min. The cells were then washed four times with ice-cold DMEM and lysed with 500 µL of 1M NaOH. The lysate was collected and placed in a scintillation tubule along with 5 mL scintillation fluid and counted.

For immunofluorescence, LLC-PK$_1$ cells were cultured on Transwell Permeable Supports (Corning Inc.). Only polarized cells were imaged, and polarization occurred 5-7 days after cells reached confluence. The cells were fixed using 4% paraformaldehyde and permeabilized using 0.1% Triton X 100. The cells were then blocked with 5% goat serum and the primary antibody was applied (anti-BCRP; Millipore Corp., clone BXP-21 at 1:100). An anti-mouse Cy3 (Sigma) secondary antibody was used (1:200), as well as a DAPI nuclear stain (Vector Labs). The cells were imaged using a confocal laser scanning microscope (Zeiss model LSM510) at 40X. Z slices were created from stacked images using the LSM Image Browser (Zeiss), decimated, exported to Image J (National Institutes of Health) and flattened into one 2D image; finally the artifact raster lines resulting from the decimation were reduced using a 16 pixel 90° motion blur filter in Adobe Photoshop (Adobe Inc.).

Western Blot and Surface Biotinylation

Oocytes were pooled 4 days after injection with either mRNA or H$_2$O (10 per treatment). Ice-cold oocyte lysis buffer was added (in mM: 20 Tris-HCl, 140 NaCl, 2% Triton X 100, and protease inhibitors), and the oocytes were incubated on ice for 30 min. Then, the oocytes were homogenized and spun at 7500 rpm at 4° C. The cell lysate was then stored at –80° C. until used for the western blot. A BCRP antibody was used to probe the blot (anti-BCRP; Millipore Corp., clone BXP-21 at 1:200) and an anti-actin antibody (1:1,000) was used as a loading control. Measurement of mutant and wild-type protein expression was done by densitometry of the homodimer bands on the western blot, performed using the Multi Gauge V3.1 program (Fugi Film). For surface biotinylation experiments, 30 oocytes from each treatment were pooled and washed with ice-cold ND96 at 4° C. The oocytes were treated with sulfo-NHS-SS-biotin ND96 solution (1 mg/mL) (Pierce Biotechnology) for 1 h at 4° C., then washed in a 192 mM glycine ND96 biotin quenching solution and lysed as described above. A portion of the lysate was retained as the total protein fraction, the remainder was added to UltraLink Immobilized NeurtrAvidin Protein beads (Pierce Biotechnology) and incubated overnight at 4° C. The following day the beads were washed, eluted, and run on a SDS-page gel.

Example 2

Population-Based Study Data

Study Population

The Atherosclerosis Risk in Communities Study (ARIC) is an ongoing population-based prospective study initiated to study cardiovascular disease and its risk factors. From 1987-1989, 15,792 mostly self-reported white and black study participants were recruited by probability sampling from four U.S. communities (visit 1). See The ARIC investigators, "The Atherosclerosis Risk in Communities (ARIC) Study: Design and objectives," Am. J. Epidemiol. 129:687-702 (1989). Participants returned for three subsequent visits approximately every three years, and participants are contacted yearly by telephone. Written informed consent was obtained from all study participants, and Institutional Review Boards of the participating institutions approved the study protocols.

Genotyping

Individuals were excluded from all genotyping for non-consent (n=53) or self-reported race other than black or white (n=47). Genotyping was conducted using the TaqMan assay to genotype the SNP rs2231142 as described previously, see Dehghan A., et al., "Association of three genetic loci with uric acid concentration and risk of gout: a genome-wide association study," Lancet 372:1953-1961 (2008), and genome-wide association data were obtained from the Affymetrix 6.0 array. For TaqMan genotyping of the rs2231142 variant, 11,440 white and 4,252 black participants were genotyped using the functionally tested TaqMan Drug Metabolizing Enzyme (DME) assay (Applied Biosystems). PCR product was amplified using 0.9 µM of each of the forward and reverse primers, 0.2 µM of each of the sequence-specific probes, 3 ng DNA, and 1×TaqMan Universal PCR Master Mix containing AmpliTaq Gold DNA Polymerase in a 5.5-µL reaction volume. Primer and sequence-specific probes are proprietary to Applied Biosystems. After an initial step of 10 min at 95° C. to activate the AmpliTaq Gold, the products were amplified using 50 cycles of 15 s at 92° C. and 90 s at 60° C. Allele detection and genotype calling were performed using the ABI 7900HT and the Sequence Detection System software (Applied Biosystems). Genotyping was successful in 97.3%. Reproducibility in a set of 313 blind duplicates was >99% with a kappa-coefficient of 0.96 indicating excellent agreement; internal lab reproducibility was 100%. Genotype distributions conformed to Hardy-Weinberg expectations in both white and black study participants (P>0.1, exact test).

GWAS genotyping was performed using the Affymetrix 6.0 genotyping assay on 8,861 white study participants. Genomic DNA was hybridized in accordance with the manufacturer's standard recommendations, and genotypes were determined using the Birdseed clustering algorithm. Individual samples were filtered to ensure genotyping quality, and 734 out of 8,861 samples were removed in data-cleaning steps for sex mismatch, discordance with previously genotyped markers, first-degree relative of an included individual, and genetic outlier based on allele sharing and principal components analyses. See Purcell S., et al., "PLINK: A tool set for whole-genome association and population based linkage analyses," Am. J. Hum. Genet. 81:559-575 (2007); Price A. L., et al., "Principal components analysis corrects for stratification in genome-wide association studies," Nat. Genet. 38:904-909 (2006).

Finally, individuals were excluded from analyses for missing outcome or covariates, and the final study sample for rs2231142 genotyped by TaqMan consisted of 10,902 white and 3,881 black individuals for the urate analyses and 8,489 white and 2,350 blacks for the analyses of gout. In the GWAS analyses, both genotype information on 2,557,232 genotyped and imputed SNPs and phentoype information was available for 8,092 white individuals for the urate analyses and 6,540 for gout. Of the 8,092 individuals with GWAS data, 7,768 had data on rs2231142 by TaqMan available. Concordance of genotypes at rs2231142 obtained by TaqMan or imputed from the GWAS data was 98%.

Genotype Imputation

For imputation, 602,642 high-quality SNPs with call rate greater than or equal to 95%, minor allele frequency greater than or equal to 1%, and conformation to Hardy-Weinberg expectations (P≥$10^{-5}$) were used. Imputation was conducted using a Hidden Markov Model as implemented in MACH to a set of 2,557,232 high-quality polymorphic HapMap SNPs. For imputation, genotype data from each sample were combined with the HapMap CEU samples. The software MACHv1.0.16 was used to infer unobserved genotypes probabilistically based on identification of shared haplotype stretches between the study sample and the HapMap CEU reference individuals [release 21 (build 35)]. Imputation results are then summarized for each genotype as an "allele dosage," a fractional value between 0 and 2, corresponding to the expected number of copies of the minor allele at that SNP.

Outcome Measures

Uric acid was measured in serum at the baseline visit using an uricase method. See Iribarren C., et al., "Correlates of uric acid and its association with asymptomatic carotid atherosclerosis: the ARIC Study. Atherosclerosis Risk in Communities," *Ann. Epidemiol.* 6:331-340 (1996). Measurements of uric acid in 40 individuals were repeated greater than or equal to one week apart; the reliability coefficient was 0.91 and the coefficient of variation was 7.2%. See Eckfeldt J. H., Chambless L. E., Shen Y. L., "Short-term, within-person variability in clinical chemistry test results. Experience from the Atherosclerosis Risk in Communities Study," *Arch. Pathol. Lab. Med.* 118:496-500 (1994). Gout was self-reported at study visit 4 in answer to the question "were you ever told you had gout." At a physiologic pH of 7.4, 98% of uric acid is present in its ionized form, urate. Therefore, serum urate levels are referenced rather than serum uric acid levels throughout this disclosure.

Statistical Analyses

For the analyses of rs2231142 genotyped by TaqMan, differences in mean urate levels by genotype were evaluated using simple linear regression. Due to the low minor allele frequency of 3%, the genotype groups GT and TT were pooled among black participants. Adjusted differences in mean urate levels were tested using multivariable adjusted linear regression, assuming an additive genetic model (P trend). Prevalence of gout was graphed and crude and multivariable adjusted odds of gout were evaluated using logistic regression in both whites and blacks. For analyses of GWAS data, mean serum urate levels were modeled using multivariable adjusted residuals in linear regression.

Covariates in all regression models were age, sex, study site, BMI, antihypertensive treatment (yes/no), and alcohol consumption (g/week) at the time of uric acid measurement or ascertainment of gout. See Dehghan A., et al., "Association of three genetic loci with uric acid concentration and risk of gout: a genome-wide association study," *Lancet* 372:1953-1961 (2008). All analyses were conducted separately by self-reported race and used an additive genetic model. The genomic control parameter for the GWAS analyses of serum urate levels across the entire genome was 1.02, indicating no substantial inflation of the test statistics.

Given the a priori hypothesis and prior evidence, see Dehghan et al., supra, the statistical significance threshold for the association analyses of rs2231142, and serum urate levels and gout was set at $\alpha=0.05$. In the analyses of the GWAS data, 601 additional SNPs at 88.9-89.5 Mb (Build 36) on chromosome 4 were analyzed, and the analyses were repeated conditional on genotype at rs2231142. The significance threshold for these analyses was set at $\alpha=8\times10^{-5}$, which corresponds to a Bonferroni correction for testing 601 independent markers. Population attributable risk (PAR) was calculated using the formula:

$$PAR(\%) = [\Sigma(p_i)(RR_i-1)/[1+\Sigma(p_i)(RR_i-1)]]\times 100$$

where $p_i$ corresponds to the proportion of individuals exposed to the risk allele (separate groups for heterozygotes and risk homozygotes) among those without gout, and $RR_i$ is estimated by the respective multivariable adjusted odds ratio of gout. See Yates J. R., et al., Complement C3 variant and the risk of age-related macular Degeneration," *N Engl. J. Med.* 357:553-561 (2007). As gout is a common disease, analyses were repeated using the prevalence ratio rather than the odds ratio of gout to obtain a conservative estimate of PAR which was 10% as compared to 13% using the odds ratio.

Single SNP analyses were conducted using Stata, and GWAS analyses were performed using the ProbABEL package from the ABEL set of programs (http://mga.bionet.nsc.ru/yurii/ABEL/), see Aulchenko Y. S., Ripke S., Isaacs A., van Duijn C. M., "GenABEL: an R library for genome-wide association analysis," *Bioinformatics* 23:1294-1296 (2007), and the statistical software R.

All publications, patent applications, patents, and other references are herein incorporated by reference to the same extent as if each publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

The following publications, patent applications, patents, as well as other references mentioned in the specification, are indicative of the level of those skilled in the art to which the presently disclosed subject matter pertains.

Anzai N., Kanai Y., Endou H., "New insights into renal transport of urate," *Curr. Opin. Rheumatol.* 19:151-157 (2007).

Yang Q., et al. "Genome-wide search for genes affecting serum uric acid levels: The Framingham Heart Study," *Metabolism* 54:1435-1441 (2005).

Lawrence R. C., et al., "Estimates of the prevalence of arthritis and other rheumatic conditions in the United States, Part II," *Arthritis Rheum.* 58:26-35 (2008).

Dehghan A., et al., "Association of three genetic loci with uric acid concentration and risk of gout: a genome-wide association study," *Lancet* 372:1953-1961 (2008).

Doyle L. A., et al., "A multidrug resistance transporter from human MCF-7 breast cancer cells," *Proc. Natl. Acad. Sci. USA* 95:15665-15670 (1998).

Polgar O., Robey R. W., Bates S. E., "ABCG2: structure, function and role in drug Response," *Expert Opin. Drug Metab. Toxicol.* 4:1-15 (2008).

Van Aubel R. A., Smeets P. H., van den Heuvel J. J., Russel F. G., "Human organic anion transporter MRP4 (ABCC4) is an efflux pump for the purine end metabolite urate with multiple allosteric substrate binding sites," *Am. J. Physiol. Renal. Physiol.* 288:F327-333 (2005).

Huls M., et al., "The breast cancer resistance protein transporter ABCG2 is expressed in the human kidney proximal tubule apical membrane," *Kidney Int* 73:220-225 (2008).

The ARIC investigators, "The Atherosclerosis Risk in Communities (ARIC) Study: Design and objectives," *Am. J. Epidemiol.* 129:687-702 (1989).

Krishnamurthy P., Schuetz J. D., "Role of ABCG2/BCRP in biology and medicine," *Annu. Rev. Pharmacol. Toxicol.* 46:381-410 (2006).

Krishnan E., Lienesch D., Kwoh C. K., "Gout in ambulatory care settings in the United States," *J. Rheumatol.* 35:498-501 (2008).

Becker M. A., et al., "Febuxostat compared with allopurinol in patients with hyperuricemia and gout," *N. Engl. J. Med.* 353:2450-2461 (2005).

Schumacher H. R., Jr., et al., "Effects of febuxostat versus allopurinol and placebo in reducing serum urate in subjects with hyperuricemia and gout: A 28-week, phase III, randomized, double-blind, parallel-group trial" *Arthritis Rheum.* 59:1540-1548 (2008).

Donnelly P., "Progress and challenges in genome-wide association studies in Humans," *Nature* 456:728-731 (2008).

McCarthy M. I., et al., "Genome-wide association studies for complex traits: Consensus, uncertainty and challenges," *Nat. Rev. Genet.* 9:356-369 (2008).

Zeuthen T., Zeuthen E., Klaerke D. A., "Mobility of ions, sugar, and water in the cytoplasm of *Xenopus* oocytes expressing Na+-coupled sugar transporters (SGLT1)," *J. Physiol.* 542:71-87 (2002).

Purcell S., et al., "PLINK: A tool set for whole-genome association and population based linkage analyses," *Am. J. Hum. Genet.* 81:559-575 (2007).

Price A. L., et al., "Principal components analysis corrects for stratification in genome-wide association studies," *Nat. Genet.* 38:904-909 (2006).

Iribarren C., Folsom A. R., Eckfeldt J. H., McGovern P. G., Nieto F. J., "Correlates of uric acid and its association with asymptomatic carotid atherosclerosis: the ARIC Study. Atherosclerosis Risk in Communities," *Ann. Epidemiol.* 6:331-340 (1996).

Eckfeldt J. H., Chambless L. E., Shen Y. L., "Short-term, within-person variability in clinical chemistry test results. Experience from the Atherosclerosis Risk in Communities Study," *Arch. Pathol. Lab. Med.* 118:496-500 (1994).

Yates J. R., et al., Complement C3 variant and the risk of age-related macular Degeneration," *N. Engl. J. Med.* 357:553-561 (2007).

Aulchenko Y. S., Ripke S., Isaacs A., van Duijn C. M., "GenABEL: an R library for genome-wide association analysis," *Bioinformatics* 23:1294-1296 (2007).

Enomoto A., et al., "Molecular identification of a renal urate anion exchanger that regulates blood urate levels," *Nature* 417:447-452 (2002).

Li S., et al., "The GLUT5 Gene Is Associated with Serum Uric Acid Levels in Sardinia and Chianti Cohorts," *PLoS Genet.* 3:e194 (2007).

Wallace C., et al., "Genome-wide association study identifies genes for biomarkers of cardiovascular disease: serum urate and dyslipidemia," *Am. J. Hum. Genet.* 82:139-149 (2008).

Doring A., et al., "SLC2A9 influences uric acid concentrations with pronounced sex-specific effects," *Nat. Genet.* 40:430-436 (2008).

Vitart V., et al., "SLC2A9 is a newly identified urate transporter influencing serum urate concentration, urate excretion and gout," *Nat. Genet.* 40:437-442 (2008).

Matsuo H., et al., "Mutations in Glucose Transporter 9 Gene SLC2A9 Cause Renal Hypouricemia," *Am. J. Hum. Genet.* 83:744-751 (2008).

Enomoto A., Endou H., "Roles of organic anion transporters (OATs) and a urate transporter (URAT1) in the pathophysiology of human disease," *Clin. Exp. Nephrol.* 9:195-205 (2005).

Rizwan A. N., Burckhardt G., "Organic anion transporters of the SLC22 family: biopharmaceutical, physiological, and pathological roles," *Pharm. Res.* 24:450-470 (2007).

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method of screening for an activator of human ATP-binding cassette, sub-family G, 2 (ABCG2) comprising the steps of
    a. incubating a cell expressing a mutant ABCG2 exhibiting decreased transport activity relative to wildtype ABCG2 with a substrate specific for ABCG2;
    b. contacting the cell with one or more candidate agents;
    c. measuring an efflux of substrate from the cell or a concentration of substrate in the cell, wherein an increase in the efflux of substrate from the cell or a decrease in the concentration of substrate in the cell determines whether the one or more candidate agents is an activator of ABCG2.

2. The method of claim 1 further comprising the step of comparing the measurement of an efflux of substrate from the cell or a concentration of substrate in the cell to a measurement of a cell not contacted with the candidate agent.

3. The method of claim 1, wherein the mutant ABCG2 is the rs2231442(Q141K) variant.

4. The method of claim 1, wherein the substrate is labeled.

5. The method of claim 4, wherein the labeled substrate is C-14 uric acid.

6. The method of claim 1, wherein the cell expressing mutant ABCG2 further expresses firefly luciferase (fLuc).

7. The method of claim 6, wherein the substrate is D-luciferin.

8. A method of screening for an activator of ABCG2 comprising the steps of
    a. incubating a cell expressing ABCG2 with uric acid or with D-luciferin;
    b. contacting the cell with one or more candidate agents;
    c. measuring an efflux of uric acid or firefly luciferase from the cell, wherein an increase in the efflux of uric acid or firefly luciferase from the cell determines whether the one or more candidate agents is an activator of ABCG2.

9. The method of claim 8 further comprising the step of comparing the measurement of an efflux of uric acid or firefly luciferase from the cell to a measurement of a cell not contacted with the candidate agent.

10. A method of screening for an activator of ABCG2 comprising the steps of
    a. incubating a cell expressing ABCG2 with uric acid or with D-luciferin;
    b. contacting the cell with one or more candidate agents;
    c. measuring a concentration of uric acid or firefly luciferase in the cell, wherein a decrease in the concentration of uric acid or firefly luciferase in the cell determines whether the one or more candidate agents is an activator of ABCG2.

11. The method of claim 10 further comprising the step of comparing the measurement of a concentration of uric acid or firefly luciferase in the cell to a measurement of a cell not contacted with the candidate agent.

12. The method of claim 8, wherein ABCG2 is wildtype ABCG2.

13. The method of claim 8, where ABCG2 is a mutant ABCG2 exhibiting decreased transport activity relative to wildtype ABCG2.

14. The method of claim 13, wherein mutant ABCG2 is the rs2231442(Q141K) variant.

15. The method of claim 8, wherein the uric acid is labeled.

16. The method of claim 15, wherein the labeled uric acid is C-14 uric acid.

17. A method of screening for an activator of ABCG2, the method comprising contacting a cell expressing ABCG2 with one or more candidate agents and measuring an efflux of uric acid from the cell or a concentration of uric acid in the cell, wherein an increase in the efflux of uric acid from the cell or a decrease in the concentration of uric acid in the cell determines whether the one or more candidate agents is an activator of ABCG2.

18. The method of claim 17 further comprising the step of comparing the measurement of an efflux of uric acid from the cell or a concentration of uric acid in the cell to a measurement of a cell not contacted with the candidate agent.

19. The method of claim 17, wherein ABCG2 is wildtype ABCG2.

20. The method of claim 17, where ABCG2 is a mutant ABCG2 exhibiting decreased transport activity relative to wildtype ABCG2.

21. The method of claim 20, wherein mutant ABCG2 is the rs2231442(Q141K) variant.

22. The method of claim 17, wherein the one or more candidate agents are small molecules.

23. The method of claim 17, wherein the uric acid is C-14 uric acid.

24. The method of claim 10, wherein ABCG2 is wildtype ABCG2.

25. The method of claim 10, where ABCG2 is a mutant ABCG2 exhibiting decreased transport activity relative to wildtype ABCG2.

26. The method of claim 25, wherein mutant ABCG2 is the rs2231442(Q141K) variant.

27. The method of claim 10, wherein the uric acid is labeled.

28. The method of claim 27, wherein the labeled uric acid is C-14 uric acid.

* * * * *